(12) United States Patent
Kamal et al.

(10) Patent No.: US 8,153,627 B2
(45) Date of Patent: Apr. 10, 2012

(54) QUINAZOLINE LINKED PYRROLO[2,1-C][1,4]BENZODIAZEPINE HYBRIDS AS POTENTIAL ANTICANCER AGENTS AND PROCESS FOR THE PREPARATION THEREOF

(75) Inventors: Ahmed Kamal, Andhra Pradesh (IN); Bandari Rajendra Prasad, Andhra Pradesh (IN); Adla Malla Reddy, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 12/920,654

(22) PCT Filed: Oct. 31, 2008

(86) PCT No.: PCT/IN2008/000712
§ 371 (c)(1),
(2), (4) Date: Sep. 2, 2010

(87) PCT Pub. No.: WO2009/109984
PCT Pub. Date: Sep. 11, 2009

(65) Prior Publication Data
US 2011/0046111 A1   Feb. 24, 2011

(30) Foreign Application Priority Data
Mar. 5, 2008   (IN) .............................. 518/DEL/2008

(51) Int. Cl.
*C07D 487/04*   (2006.01)
*A61K 31/5517*   (2006.01)
*A61P 35/00*   (2006.01)

(52) U.S. Cl. ........................................ 514/220; 540/496

(58) Field of Classification Search .................. 540/496; 514/220
See application file for complete search history.

(56) References Cited

FOREIGN PATENT DOCUMENTS

| WO | 2004/087712 A1 | 10/2004 |
| WO | 2004/087716 A1 | 10/2004 |
| WO | 2006/003670 A1 | 1/2006 |
| WO | 2007/054954 A1 | 5/2007 |
| WO | 2008/020456 A2 | 2/2008 |

OTHER PUBLICATIONS

NSC724010—Compound Summary (CID406092) Internet Citation, Mar. 27, 2005, XP002515700 Retrieved from the Internet: URL:http://pubchem.ncbi.nlm.nih.gov/summary/summary.cgi?cid=406092> [retrieved on Feb. 18, 2009] Bioactivity Analysis Compound is shown to active against NIC SR Leukemia and NIC-H522 cell lines.
International Search Report: mailed Apr. 3, 2009; Appln. PCT/IN2008/000712.

*Primary Examiner* — Bruck Kifle
(74) *Attorney, Agent, or Firm* — Ladas & Parry LLP

(57) ABSTRACT

The present invention provides a compound of general formula 5, useful as potential antitumour agents against human cancer cell lines. The present invention further provides a process for the preparation of pyrrolo[2,1-c][1,4]benzodiazepine hybrids of general formula (5): wherein n=3, 4, 5, 6, 8 and wherein R1 and R² is selected from the group consisting of $R^1$=H, $R^2$=H or $R^1$=$CH_3O$, R2=$CH_3O$ or $R^1$=$CH_3O$ and $R^2$=$C_2H_5O$.

(I)

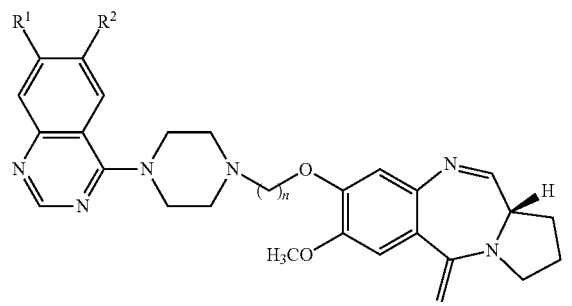

9 Claims, No Drawings

QUINAZOLINE LINKED PYRROLO[2,1-C][1,4]BENZODIAZEPINE HYBRIDS AS POTENTIAL ANTICANCER AGENTS AND PROCESS FOR THE PREPARATION THEREOF

FIELD OF THE INVENTION

The present invention relates to quinazoline linked pyrrolo[2,1-c][1,4]benzodiazepine hybrids and a process for the preparation thereof. More particularly it relates to 7-methoxy-8-{substituted(4-piperazinoquinazoline)alkyl]oxy}-(11aS)-1,2,3,11a-tetrahydro-5H-pyrrolo[2,1-c][1,4]benzodiazepine-5-one with aliphatic chain length variations useful as anticancer agent. The structural formula of these quinazoline linked pyrrolo[2,1-c][1,4]benzodiazepines hybrids is given below.

Formula 5

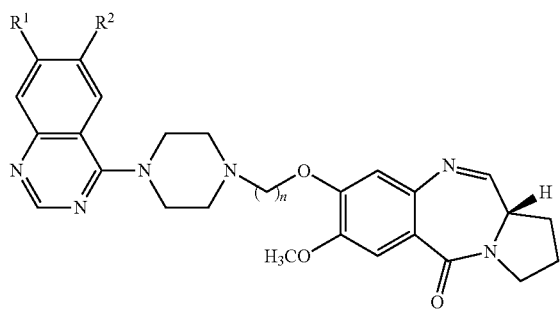

and where n=3-6,8 and wherein $R^1$ and $R^2$ is selected from the group consisting of $R^1$=H, $R^2$=H or $R^1$=CH$_3$O, $R^2$=CH$_3$O or $R^1$=CH$_3$O and $R^2$=C$_2$H$_5$O

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. J. Antibiot., 1980, 33, 665.; Kohn, K. W. and Speous, C. L. J. Mol. Biol., 1970, 51, 551.; Hurley, L. H.; Gairpla, C. and Zmijewski, M. Biochem. Biophys. Acta., 1977, 475, 521.; Kaplan, D. J. and Hurley, L. H. Biochemistry, 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S, and Hurley, L. H. J. Org. Chem. 1996, 61, 8141).

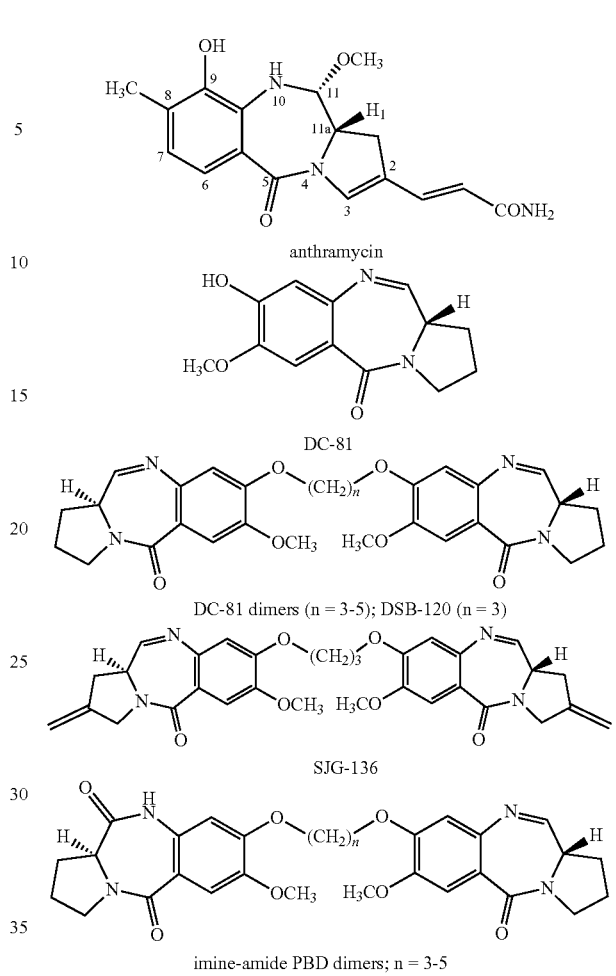

Recently, PBD dimers have been developed that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. J. Med. Chem. 2001, 44, 737). A non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. J. Med. Chem. 2002, 45, 4679). Recently, some new pyrrolobenzodiazepine (PBD) hybrids have been synthesized that have significant DNA binding ability and potent antitumour activity. (Kamal, A.; Srinivas; O.; Ramulu, P.; Ramesh, G.; Kumar, P. P. Bioorg. Med. Chem. Lett. 2003, 13, 3577).

Naturally occurring pyrrolo[2,1-c][1,4]benzodiazepines belong to a group of antitumour antibiotics derived from Streptomyces species. Recently, there is much impetus for the PBD systems as they can recognize and bind to specific sequence of DNA. Examples of naturally occurring PBDs include anthramycin, DC-81, tomaymycin, sibiromycin and neothramycin.

However, the clinical efficacy for these antibiotics is hindered by several limitations, such as poor water solubility, cardio toxicity, development of drug resistance and metabolic inactivation.

OBJECTIVES OF THE INVENTION

The main objective of the present invention is to provide novel quinazoline linked pyrrolo[2,1-c][1,4]benzodiazepine hybrids, useful as antitumour agents.

Yet another object of this invention is to provide a process for the preparation of novel quinazoline linked pyrrolo[2,1-c][1,4]benzodiazepine hybrids.

SUMMARY OF THE INVENTION

Accordingly the present invention provides a novel quinazoline linked pyrrolo-[2,1-c][1,4]benzodiazepine hybrid of general formula 5

Formula 5

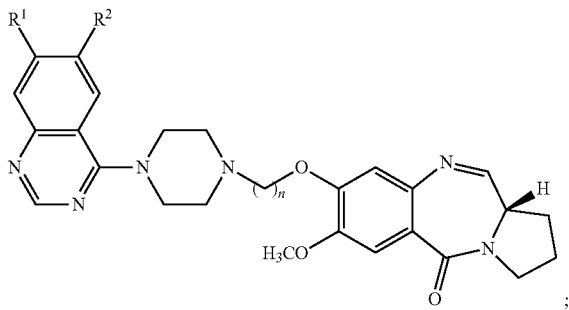

wherein n=3-6, 8 and wherein $R^1$ and $R^2$ is selected from the group consisting of $R^1$=H, $R^2$=H or $R^1$=$CH_3O$, $R^2$=$CH_3O$ or $R^1$=$CH_3O$ and $R^2$=$C_2H_5O$ In an embodiment of the present invention the novel quinazoline linked pyrrolo[2,1-c][1,4]benzodiazepine hybrid as claimed in claim 1 is represented by the group of the following compounds:

7-Methoxy-8-{[-3-(4-piperazinoquinazoline]propyl}-oxy-(11aS)-1,2,3,11a-5H-pyrrolo[2,1-c][1,4]benzodiazepin-5-one (5a)

7-Methoxy-8-{[-4-(4-piperazinoquinazoline]butyl}-oxy-(11aS)-1,2,3,11a-5H-pyrrolo[2,1-c][1,4]benzodiazepin-5-one (5b);

7-Methoxy-8-{[-5-(4-piperazinoquinazoline]pentyl}-oxy-(11aS)-1,2,3,11a-5H-pyrrolo[2,1-c][1,4]benzodiazepin-5-one (5c);

7-Methoxy-8-{[-6-(4-piperazinoquinazoline]hexyl}-oxy-(11aS)-1,2,3,11a-5H-pyrrolo[2,1-c][1,4]benzodiazepin-5-one (5d);

7-Methoxy-8-{[-8-(4-piperazinoquinazoline]octyl}-oxy-(11aS)-1,2,3,11a-5H-pyrrolo[2,1-c][1,4]benzodiazepin-5-one (5e);

7-Methoxy-8-{6,7-dimethoxy[-3-(4-piperazinoquinazoline]propyl}-oxy-(11aS)-1,2,3,11a-5H-pyrrolo[2,1-c][1,4]benzodiazepin-5-one (5f);

7-Methoxy-8-{6,7-dimethoxy[-4-(4-piperazinoquinazoline]butyl}-oxy-(11aS)-1,2,3,11a-5H-pyrrolo[2,1-c][1,4]benzodiazepin-5-one (5g);

7-Methoxy-8-{6,7-dimethoxy[-5-(4-piperazinoquinazoline]pentyl}-oxy-(11aS)-1,2,3,11a-5H-pyrrolo[2,1-c][1,4]benzodiazepin-5-one (5h);

7-Methoxy-8-{6,7-dimethoxy[-6-(4-piperazinoquinazoline]hexyl}-oxy-(11aS)-1,2,3,11a-5H-pyrrolo[2,1-c][1,4]benzodiazepin-5-one (5i);

7-Methoxy-8-{6,7-dimethoxy[-8-(4-piperazinoquinazoline]octyl}-oxy-(11aS)-1,2,3,11a-5H-pyrrolo[2,1-c][1,4]benzodiazepin-5-one (5j);

7-Methoxy-8-{7-ethoxy,6-methoxy[-3-(4-piperazinoquinazoline]propyl}-oxy-(11aS)-1,2,3,11a-5H-pyrrolo[2,1-c][1,4]benzodiazepin-5-one (5k);

7-Methoxy-8-{7-ethoxy,6-methoxy[-4-(4-piperazinoquinazoline]butyl}-oxy-(11aS)-1,2,3,11a-5H-pyrrolo[2,1-c][1,4]benzodiazepin-5-one (5l);

7-Methoxy-8-{7-ethoxy,6-methoxy[-5-(4-piperazinoquinazoline]pentyl}-oxy-(11aS)-1,2,3,11a-5H-pyrrolo[2,1-c][1,4]benzodiazepin-5-one (5m);

7-Methoxy-8-{7-ethoxy,6-methoxy[-6-(4-piperazinoquinazoline]hexyl}-oxy-(11aS)-1,2,3,11a-5H-pyrrolo[2,1-c][1,4]benzodiazepin-5-one (5n);

7-Methoxy-8-{7-ethoxy,6-methoxy [-8-(4-piperazinoquinazoline]octyl}-oxy-(11aS)-1,2,3,11a-5H-pyrrolo[2,1-c][1,4]benzodiazepin-5-one (5o)

In yet another embodiment the structural formula of the representative compounds of quinazoline linked pyrrolo[2,1-c][1,4]benzodiazepine hybrids are:

Formula 5a-e

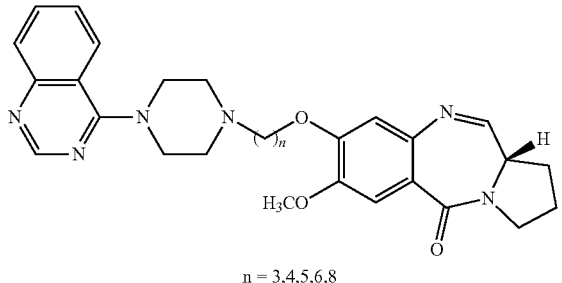

n = 3,4,5,6,8

Formula 5f-j

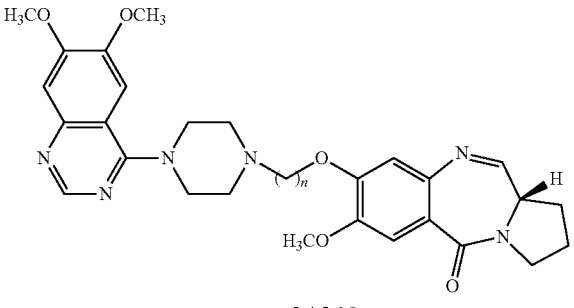

n = 3,4,5,6,8

Formula 5k-o

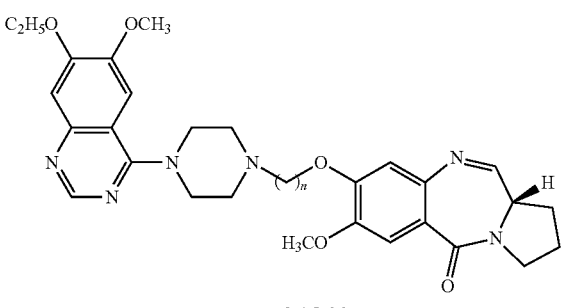

n = 3,4,5,6,8

In yet another embodiment the novel quinazoline linked pyrrolo[2,1-c][1,4]benzodiazepine hybrid exhibits an in vitro anticancer/antitumour activity against human cancer cell lines selected from the group consisting of lung (Hop-62), cervix (SiHa), breast (MCF7, Zr-75-1), colon (Colo205), prostate (DU145, PC3) and oral (DWD, HT1080) cell lines.

In yet another embodiment the concentration of quinazoline linked pyrrolo[2,1-c][1,4]benzodiazepine hybrid used for in vitro activity against Colo205 for IC50 is in the range of 12 to 80 μm, at an exposure period of at least 48 hrs.

In yet another embodiment the concentration of quinazoline linked pyrrolo[2,1-c][1,4]benzodiazepine hybrids used for in vitro activity against DU145 for IC50 is in the range of 15 to 80 μm, at an exposure period of at least 48 hrs.

In yet another embodiment the concentration of quinazoline linked pyrrolo[2,1-c][1,4]benzodiazepine hybrids used for in vitro activity against DWD for IC50 is in the range of 6 to 80 μm, at an exposure period of at least 48 hrs.

In yet another embodiment the concentration of quinazoline linked pyrrolo[2,1-c][1,4]benzodiazepine hybrids used for in vitro activity against HoP62 for IC50 is in the range of 13 to 40 μm, at an exposure period of at least 48 hrs.

In yet another embodiment the concentration of quinazoline linked pyrrolo[2,1-c][1,4]benzodiazepine hybrids used for in vitro activity against HT1080 for IC50 is in the range of 6 to 30 μm, at an exposure period of at least 48 hrs.

In yet another embodiment the concentration of quinazoline linked pyrrolo[2,1-c][1,4]benzodiazepine hybrids used for in vitro activity against MCF7 for IC50 is in the range of 23 to 80 μm, at an exposure period of at least 48 hrs.

In yet another embodiment the concentration of quinazoline linked pyrrolo[2,1-c][1,4]benzodiazepine hybrids used for in vitro activity against PC3 for IC50 is in the range of 5 to about 80 μm, at an exposure period of at least 48 hrs.

In yet another embodiment the concentration of quinazoline linked pyrrolo[2,1-c][1,4]benzodiazepine hybrids used for in vitro activity against SiHa for IC50 is in the range of 19 to about 80 μm, at an exposure period of at least 48 hrs.

In yet another embodiment the concentration of quinazoline linked pyrrolo[2,1-c][1,4]benzodiazepine hybrids used for in vitro activity against Zr-75-1 for IC50 is in the range of 16 to about 80 μm, at an exposure period of at least 48 hrs.

The present invention further provides a pharmaceutical composition comprising quinazoline linked pyrrolo[2,1-c][1,4]benzodiazepine hybrid, its derivatives, analogues, salts or mixture thereof optionally with pharmaceutically acceptable carriers, adjuvants and additives.

In yet another embodiment the quinazoline linked pyrrolo[2,1-c][1,4]benzodiazepine hybrid used is represented by a general formula 5, Formula 5

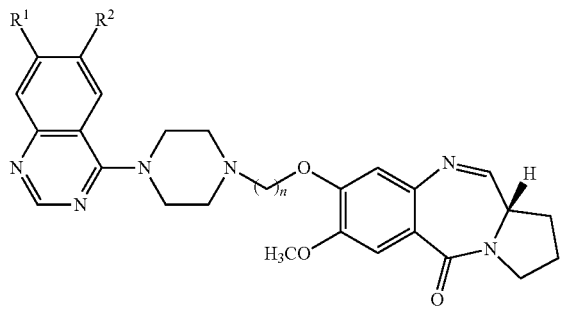

wherein n=3, 4, 5, 6, 8 and wherein $R^1$ and $R^2$ is selected from the group consisting of $R^1$=H, $R^2$=H or $R^1$=CH$_3$O, $R^2$=CH$_3$O or $R^1$=CH$_3$O and $R^2$=C$_2$H$_5$O The present invention further provides a process for the preparation of quinazoline linked pyrrolo[2,1-c][1,4]benzodiazepine hybrid of formula 5

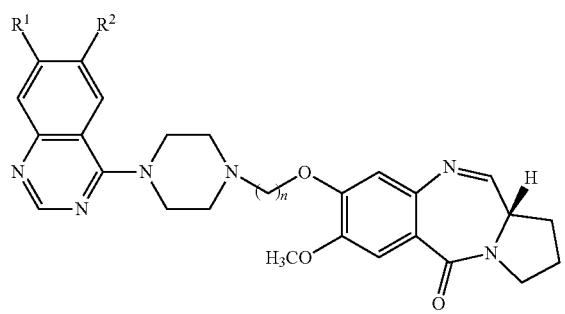

wherein n=3, 4, 5, 6, 8 and wherein $R^1$ and $R^2$ is selected from the group consisting of $R^1$=H, $R^2$=H or $R^1$=CH$_3$O, $R^2$=CH$_3$O or $R^1$=CH$_3$O and $R^2$=C$_2$H$_5$O The said process comprising the steps of:

a) reacting (2S)—N-[(n-bromoalkyloxy)-5-methoxy-2-nitrobenzoyl)]pyrrolidine-2-carboxaldehyde diethylthioacetal of formula 1

1a-e

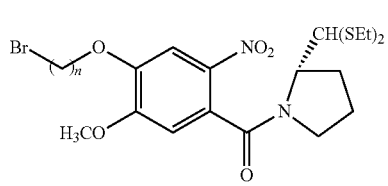

where n=3 to 6 and 8 with nonsubstituted and substituted-4-piperazinoquinazoline derivative selected from the compound of formula 2a-c 2a-c

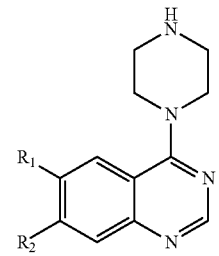

wherein $R^1$, and $R^2$ is selected from the group of consisting of H, H or CH$_3$O, CH$_3$O or CH$_3$O, C$_2$H$_5$O, in the presence of a mild inorganic base, in an aprotic organic solvent, under refluxing temperature to obtain the resultant nitro compound of formula 3, 3a-o

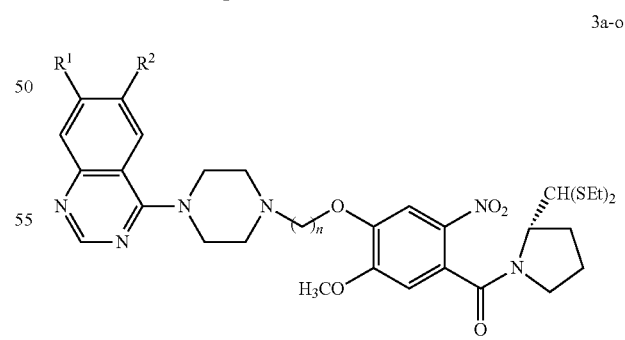

n = 3,4,5,6,8 wherein R1 and $R^2$ is selected from the group consisting of $R^1$=H, $R^2$=H or R1=CH$_3$O, $R^2$=CH$_3$O or $R^1$=CH$_3$O and $R^2$=C$_2$H$_5$O b) reducing the above said nitro compound of formula 3 obtained in step (a) with SnCl$_2$.2H$_2$O in an organic solvent, under reflux temperature and isolating the corresponding amino compound of formula 4,

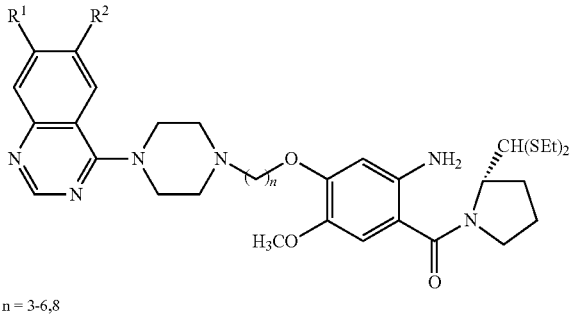

n = 3-6,8 wherein R1 and R² is selected from the group consisting of $R^1=H$, $R^2=H$ or $R^1=CH_3O$, $R^2=CH_3O$ or $R^1=CH_3O$ and $R^2=C_2H_5O$ c) reacting the above said amino compound of formula 4 obtained in step (b) with a deprotecting agent in a mixture of water and organic solvent in the presence of a mild inorganic basic compound by known method to obtain the desired compound of formula 5.

In yet another embodiment the mild inorganic base used in steps (a) is selected from the group of potassium carbonate and Acetone.

In yet another embodiment the mild inorganic base used in steps (a) is potassium carbonate.

In yet another embodiment the aprotic organic solvent used in step (a) is acetone and acetonitrile In yet another embodiment the organic solvent used in step (c) is acetonitrile and acetone In yet another embodiment the alcohol used in step (b) is selected from methanol and ethanol.

In yet another embodiment the compounds of formula 5 obtained are represented by a group of the following compounds:

7-Methoxy-8-{[-3-(4-piperazinoquinazoline]propyl}-oxy-(11aS)-1,2,3,11a-5H-pyrrolo[2,1-][1,4]benzodiazepin-5-one (5a);

7-Methoxy-8-{[-4-(4-piperazinoquinazoline]butyl}-oxy-(11aS)-1,2,3,11a-5H-pyrrolo[2,1-c][1,4]benzodiazepin-5-one (5b);

7-Methoxy-8-{[-5-(4-piperazinoquinazoline]pentyl}-oxy-(11aS)-1,2,3,11a-5H-pyrrolo[2,1-c][1,4]benzodiazepin-5-one (5c);

7-Methoxy-8-{[-6-(4-piperazinoquinazoline]hexyl}-oxy-(11aS)-1,2,3,11a-5H-pyrrolo[2,1-c][1,4]benzodiazepin-5-one (5d);

7-Methoxy-8-{[-8-(4-piperazinoquinazoline]octyl}-oxy-(11aS)-1,2,3,11a-5H-pyrrolo[2,1-c][1,4]benzodiazepin-5-one (5e);

7-Methoxy-8-{6,7-dimethoxy[-3-(4-piperazinoquinazoline]propyl}-oxy-(11aS)-1,2,3,11a-5H-pyrrolo[2,1-c][1,4]benzodiazepin-5-one (5f);

7-Methoxy-8-{6,7-dimethoxy[-4-(4-piperazinoquinazoline]butyl}-oxy-(11aS)-1,2,3,11a-5H-pyrrolo[2,1-c][1,4]benzodiazepin-5-one (5g);

7-Methoxy-8-{6,7-dimethoxy[-5-(4-piperazinoquinazoline]pentyl}-oxy-(11aS)-1,2,3,11a-5H-pyrrolo[2,1-c][1,4]benzodiazepin-5-one (5h);

7-Methoxy-8-{6,7-dimethoxy[-6-(4-piperazinoquinazoline]hexyl}-oxy-(11aS)-1,2,3,11a-5H-pyrrolo[2,1-c][1,4]benzodiazepin-5-one (5i);

7-Methoxy-8-{6,7-dimethoxy[-8-(4-piperazinoquinazoline]octyl}-oxy-(11aS)-1,2,3,11a-5H-pyrrolo[2,1-c][1,4]benzodiazepin-5-one (5j);

7-Methoxy-8-{7-ethoxy,6-methoxy[-3-(4-piperazinoquinazoline]propyl}-oxy-(11aS)-1,2,3,11a-5H-pyrrolo[2,1-c][1,4]benzodiazepin-5-one (5k);

7-Methoxy-8-{7-ethoxy,6-methoxy[-4-(4-piperazinoquinazoline]butyl}-oxy-(11aS)-1,2,3,11a-5H-pyrrolo[2,1-c][1,4]benzodiazepin-5-one (5l);

7-Methoxy-8-{7-ethoxy,6-methoxy[-5-(4-piperazinoquinazoline]pentyl}-oxy-(11aS)-1,2,3,11a-5H-pyrrolo[2,1-c][1,4]benzodiazepin-5-one (5m);

7-Methoxy-8-{7-ethoxy,6-methoxy[-6-(4-piperazinoquinazoline]hexyl}-oxy-(11aS)-1,2,3,11a-5H-pyrrolo[2,1-c][1,4]benzodiazepin-5-one (5n);

7-Methoxy-8-{7-ethoxy,6-methoxy[-8-(4-piperazinoquinazoline]octyl}-oxy-(11aS)-1,2,3,11a-5H-pyrrolo[2,1-c][1,4]benzodiazepin-5-one (5o);

In still another embodiment the quinazoline linked pyrrolo[2,1-c][1,4]benzo-diazepine hybrid of formula 5a-o exhibits an in vitro anticancer/antitumour activity against human cancer cell lines selected from the group consisting of lung, cervix, breast, colon, prostate and oral cell lines.

DETAILED DESCRIPTION OF THE INVENTION

Accordingly, the present invention provides a process for preparation of pyrrolo[2,1-c][1,4]benzodiazepine hybrids of formula 5

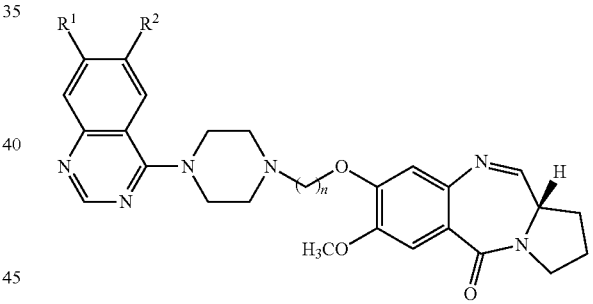

where n=3-6, 8, and wherein R1 and R² is selected from the group consisting of $R^1=H$, $R^2=H$ or $R^1=CH_3O$, $R^2=CH_3O$ or $R^1=CH_3O$ and $R^2=C_2H_5O$ and which comprises reacting substituted and unsubstituted 4-piperazinoquinazoline derivative of formula 2 with (2S)—N-[(n-bromoalkyloxy)-5-methoxy-2-nitrobenzoyl)]pyrrolidine-2-carboxaldehyde diethylthioacetal of formula 1 in presence of $CH_3COCH_3/K_2CO_3$ for a period of 48 h resulting in isolation of (2S)—N-{n-[substituted or un-substituted (4-piperazinoquinazoline]alkyl-oxy-5-methoxy-2-nitrobenzoyl}pyrrolidine-2-carboxaldehyde diethyl thioacetal of formula 3 by conventional methods. Reducing the above nitro compound of formula 3 with $SnCl_2.2H_2O$ in presence of organic solvent with reflux temperature, resulting with the formation of (2S)—N-{n-[4-piperazinoquinazoline]alkyloxy]}-5-methoxy-2-aminobenzoyl}pyrrolidine-2-carboxaldehyde diethylthioacetal 4. Reacting the above said amino compound of formula 4 with known deprotecting agents in a conventional manner to give novel pyrrolo[2,1-c][1,4]benzodiazepine hybrids of formula 5, where 'n' is as stated above.

The precursors, substituted 4-piperazinoquinazoline of formula 2 (Liou, J. P.; Chang, C. W.; Song, J. S.; Yang, Y. N.; Yeh, C. F.; Tseng, H. Y.; Lo, Y. K.; Chang, Y. L.; Chang, C. M.; Hsieh, H. P.; J. Med. Chem. 2002, 45, 4513-4523). and (2S)—N-(4-hydroxy-5-methoxy-2-nitrobenzoyl)pyrrolidine-2-carboxaldehyde diethylthioacetal of formula 1 (Thurston, D. E.; Morris, S. J.; Hartley, J. A. Chem. Commun. 1996, 563-565) have been prepared by literature methods.

Some representative compounds of formula 5 for the present inventions are given below (5a) 7-Methoxy-8-{4-[-3-(4-piperazinoquinazoline]propyl}-oxy-(11aS)-1,2,3,11a-5H-pyrrolo[2,1-c][1,4]benzodiazepin-5-one.
(5b) 7-Methoxy-8-{4-[-3-(4-piperazinoquinazoline]butyl}-oxy-(11aS)-1,2,3,11a-5H-pyrrolo[2,1-c][1,4]benzodiazepin-5-one.
(5c) 7-Methoxy-8-{4-[-3-(4-piperazinoquinazoline]pentyl}-oxy-(11aS)-1,2,3,11a-5H-pyrrolo[2,1-c][1,4]benzodiazepin-5-one.
(5d) 7-Methoxy-8-{4-[-3-(4-piperazinoquinazoline]hexyl}-oxy-(11aS)-1,2,3,11a-5H-pyrrolo[2,1-c][1,4]benzodiazepin-5-one.
(5e) 7-Methoxy-8-{4-[3-(4-piperazinoquinazoline]octyl}-oxy-(11aS)-1,2,3,11a-5H-pyrrolo[2,1-c][1,4]benzodiazepin-5-one.

The process for the preparation of new pyrrolo[2,1-c][1,4] benzodiazepine hybrids is disclosed and claimed in our co-pending Indian patent application no. 603/DEU2008.

These new analogues of pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property. This resulted in design and synthesis of new congeners as illustrated in Scheme-1, which comprise:

1. The ether linkage at C-8 position of DC-81 intermediates with 3-(4-hydroxy-3-methoxyphenyl)-1-(4-phenyl-3-quinolyl)-2-propen-1-one moiety.
2. Refluxing the reaction mixtures for 48 h.
3. Synthesis of C-8 linked PBD antitumour antibiotic hybrid imines.
4. Purification by column chromatography using different solvents like ethyl acetate, hexane, dichloromethane and methanol.

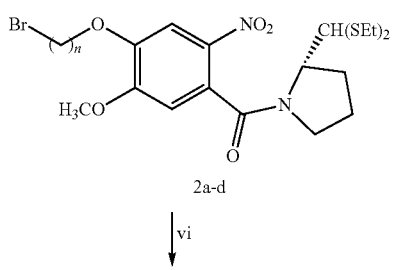

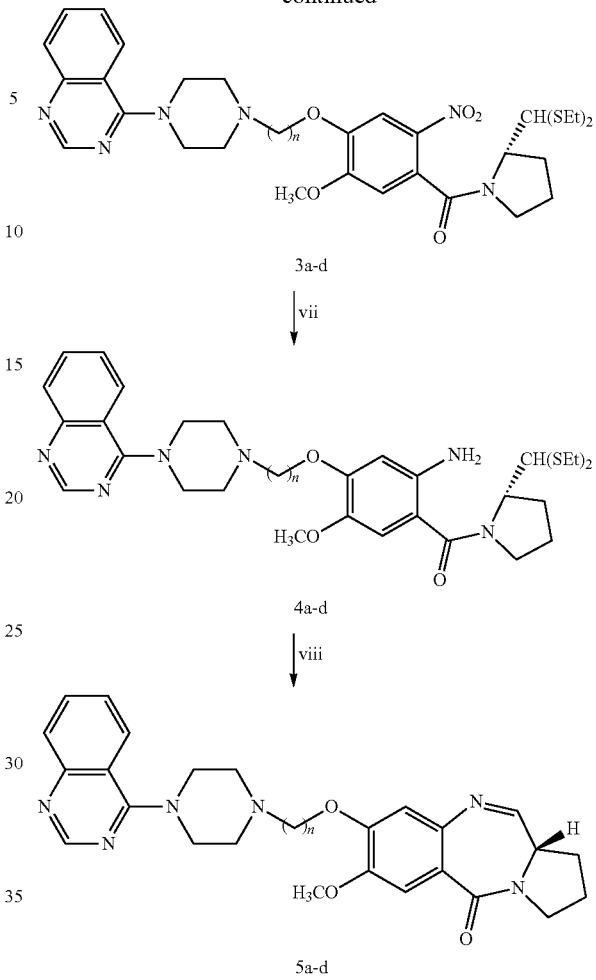

n = 3-6, 8

Reagents and conditions: (i) $SOCl_2$, $C_6H_6$, L-prolinemethyl ester hydrochloride, THF—$H_2O$, 2 h, rt, 85%; (ii) DIBAL-H, $CH_2Cl_2$, 1 h, −78° C., 71%; (iii) EtSH, TMSCl, $CH_2Cl_2$, 8 h, rt; (iv) EtSH—$BF_3OEt_2$, $CH_2Cl_2$, 12 h, rt, 75%; (v) dibromoalkanes, $K_2CO_3$, acetone, 48 h, reflux, 94-96%; (vi) compound 3, acetonitrile, 48 h, reflux, 94-96%; (vii) $SnCl_2.2H_2O$, MeOH, 2 h, reflux, 85-87%; (viii) $HgCl_2$—$CaCO_3$, $CH_3CN$—$H_2O$ (4:1), 12 h, rt, 68-71%.

| Compound | $R^1$ | $R^2$ | n |
|---|---|---|---|
| 5a | H | H | 3 |
| 5b | H | H | 4 |
| 5c | H | H | 5 |
| 5d | H | H | 6 |
| 5e | H | H | 8 |
| 5f | $CH_3O$ | $CH_3O$ | 3 |
| 5g | $CH_3O$ | $CH_3O$ | 4 |
| 5h | $CH_3O$ | $CH_3O$ | 5 |
| 5i | $CH_3O$ | $CH_3O$ | 6 |
| 5j | $CH_3O$ | $CH_3O$ | 8 |
| 5k | $CH_3O$ | $C_2H_5O$ | 3 |
| 5l | $CH_3O$ | $C_2H_5O$ | 4 |
| 5m | $CH_3O$ | $C_2H_5O$ | 5 |
| 5n | $CH_3O$ | $C_2H_5O$ | 6 |
| 5o | $CH_3O$ | $C_2H_5O$ | 8 |

The following examples are given by way of illustration and therefore should not be construed to the present limit of the scope of invention.

Example-1

(2S)—N-{4-[3-[4-Piperazinoquinazoline]propyl]oxy]-5-methoxy-2-nitrobenzoyl}pyrrolidine-2-carboxaldehyde diethylthioacetal (3a)

To a solution of compound (2S)—N-[-4-(3-Bromopropoxy)-5-methoxy-2-nitrobenzoyl]pyrrolidine-2-carboxaldehyde diethylthioacetal (1a) 521 mg, 1.0 mmol) in dry acetonitrile (15 ml) was added, 4-piperazino-quinazoline (2a) (214 mg, 1.0 mmol) followed by anhydrous $K_2CO_3$ (690 mg, 2.0 mmol) and the reaction mixture was refluxed for 48 hrs. After the completion of the reaction as indicated by TLC, EtOAc:hexane (7:3), the reaction mixture was concentrated under reduced pressure and then extracted with ethyl acetate. This was concentrated under reduced pressure to obtain the crude product which was further purified by column chromatography on silica gel eluting with EtOAc:hexane (9:1) to obtain the pure compound 2S)—N-{4-[3-[4-piperazinoquinazoline]propyl]oxy]-5-methoxy-2-nitrobenzoyl}pyrrolidine-2-carboxaldehyde diethylthioacetal 3a as yellow solid (560 mg, 85%).

$^1$H NMR ($CDCl_3$) δ 1.32-1.40 (m, 6H), 1.75-2.30 (m, 6H), 2.61-2.86 (m, 6H), 3.21-3.30 (m, 6H), 3.80-3.86 (t, 4H, J=7.32 Hz), 3.96 (s, 3H), 4.19-4.24 (t, 2H), 4.66-4.74 (m, 1H), 4.85-4.87 (d, 1H, J=3.96), 6.82 (s, 1H), 7.42-7.47 (t, 1H, J=6.63 Hz), 7.70-7.75 (m, 2H), 7.86-7.91 (m, 2H); 8.71 (s, 1H).
MS (FAB) 655.27 [M+H].

(2S)—N-{-4-[3-[4-piperazinoquinazoline]propyl]oxy]-5-methoxy-2-aminobenzoyl}pyrrolidine-2-carboxaldehyde diethylthioacetal (4a)

The compound 3a (655 mg, 10 mmol) dissolved in methanol (20 ml) and added $SnCl_2.2H_2O$ (1.125 g, 5 0 mmol) was refluxed for 2 h or until the TLC indicated that reaction was complete. The methanol was evaporated under vacuum and the aqueous layer was then adjusted to pH 8 with 10% $NaHCO_3$ solution and then extracted with ethyl acetate (2×30 ml). The combined organic phase was dried over $Na_2SO_4$ and evaporated under vacuum to afford the amino diethyl thioacetal, 4a, which, due to potential stability problems, was used directly in the next step (612 mg, 97%).

7-Methoxy-8-{3-[4-piperazinoquinazoline]propyl}-oxy-(11aS)-1,2,3,11a-5H-pyrrolo[2,1-c][1,4]benzodiazepin-5-one (5a)

A solution of 4a (625 mg, 10 mmol), $HgCl_2$ (678 mg, 2.5 mmol) and $CaCO_3$ (250 mg, 2.5 mmol) in acetonitrile-water (4:1) was stirred at room temperature for 12 h until the completion of the reaction as shown by TLC (EtOAc). The organic layer was evaporated in vacuum and the residue was diluted with EtOAc. To this, saturated $NaHCO_3$ was added slowly at room temperature and the mixture was filtered through a celite bed and washed with ethyl acetate. The filtrate was evaporated in vacuum to get crude compound 5a, which was further purified by column chromatography on silica gel eluting first with ethyl acetate to remove traces of mercuric salts and then with $CHCl_3$:methanol (9:1) (392 mg, 62%).

$^1$H NMR ($CDCl_3$) δ 1.25-1.42 (m, 4H), 1.64-1.88 (m, 4H), 2.02-2.20 (m, 3H), 2.28-2.39 (m, 2H), 2.63-2.78 (m, 4H), 3.80-3.91 (m, 2H), 3.96 (s, 3H), 4.18-4.24 (t, 2H, J=6.73 Hz)), 7.42-7.56 (m, 2H), 7.67-7-79 (m, 2H), 7.87-7.94 (m, 2H), 8.74 (s, 1H); MS (FAB) 500 [M+H]$^+$.

Example-2

(2S)—N-{4-[4-[4-piperazinoquinazoline]butyl]oxy]-5-methoxy-2-nitrobenzoyl}pyrrolidine-2-carboxaldehyde diethylthioacetal (3b)

The compound 3b has been prepared according to the method described for the compound 3a by employing the compounds 1b (535 mg, 10 mmol) was added anhydrous $K_2CO_3$ (690 mg, 5.0 mmol) and 4-piperazino-quinazoline (2a) (214 mg, 1.0 mmol) to afford the compound 3b (608 mg, 90%).

$^1$H NMR ($CDCl_3$) δ 1.24-1.43 (m, 6H), 1.69-2.17 (m, 6H), 2.20-2.38 (m, 6H), 2.48-2.84 (m, 6H), 3.18-3.30 (m, 4H), 3.76-3.83 (m, 4H), 3.95 (s, 3H), 4.09-4.18 (m, 2H), 4.62-4.72 (m, 1H), 4.82-4.84 (d, 1H, J=3.67), 6.78 (s, 1H), 7.38-7.46 (t, 1H, J=7.34), 7.64-7-76 (m, 3H), 7.83-7.91 (t, 1H, J=7.34 Hz), 8.69 (s, 1H).
MS (FAB) 669 [M+H]$^+$.

2S)—N-{-4-[4-[4-piperazinoquinazoline]butyl]oxy]-5-methoxy-2-amino benzoyl}pyrrolidine-2-carboxaldehyde diethyl thioacetal (4b)

The compound 4b has been prepared according to the method described for the compound 4a by employing compound 3b (669 mg, 10 mmol) to afford compound 4b (640 mg, 95%), which, due to potential stability problems, was used directly in the next step.

7-Methoxy-8-{4-[4-piperazinoquinazoline]butyl}-oxy-(11aS)-1,2,3,11a-5H-pyrrolo[2,1-c][1,4]benzodiazepin-5-one (5b)

The compound 5b was prepared according to the method described for the compound 5a employing the compound 4b (640 mg, 10 mmol) to afford the compound 5b (435 mg, 67%).

$^1$H NMR ($CDCl_3$) δ 1.25-1.42 (m, 4H), 1.64-1.88 (m, 4H), 2.02-2.20 (m, 3H), 2.28-2.39 (m, 2H), 2.63-2.78 (m, 4H), 3.80-3.91 (m, 4H), 3.96 (s, 3H), 4.18-4.24 (t, 2H, J=6.73 Hz), 7.42-7.56 (m, 2H), 7.67-7-79 (m, 2H), 7.87-7.94 (m, 2H), 8.74 (s, 1H); MS (FAB) 514 [M+H]$^+$.

Example-3

(2S)—N-{4-[5-[4-piperazinoquinazoline]pentyl]oxy]-5-methoxy-2-nitrobenzoyl}pyrrolidine-2-carboxaldehyde diethylthioacetal (3c)

The compound 3c as been prepared according to the method described for the compound 3a by employing the compounds 1c (549 mg, 10 mmol) was added anhydrous $K_2CO_3$ (690 mg, 5.0 mmol) and 4-piperazino-quinazoline (2a) (214 mg, 1.0 mmol) to afford the compound 3c (629 mg, 92%).

$^1$H NMR ($CDCl_3$) δ 1.22-1.40 (m, 6H), 1.52-1.72 (m, 4H), 1.86-1.99 (m, 6H), 2.00-2.08 (m, 2H), 2.12-2.18 (m, 4H), 2.21-2.33 (m, 2), 3.19-3.30 (m, 4H), 3.32-3.43 (m, 4H), 3.95 (s, 3H), 4.19-4.25 (t, 2H, J=6.51 Hz), 4.66-4.74 (m, 1H), 4.84-4.88 (d, 1H, j=3.98 Hz), 6.83 (s, 1H), 7.41-7.48 (m, 2H), 7.86-7.93 (m, 3H), 8.73 (s, 1H).
MS (FAB) 683 [M+H]+.

(2S)—N-{4-[5-[4-piperazinoquinazoline]pentyl]oxy]-5-methoxy-2-aminobenzoyl}pyrrolidine-2-carboxaldehyde diethylthioacetal (4c)

The compound 4c has been prepared according to the method described for the compound 4a by employing compound 3c (683 mg, 10 mmol) to afford compound 4c (654 mg, 95%), which, due to potential stability problems, was used directly in the next step.

7-Methoxy-8-{5-[4-piperazinoquinazoline]pentyl}-oxy-(11aS)-1,2,3,11a-5H-pyrrolo[2,1-c][1,4]benzodiazepin-5-one (5c)

The compound 5c was prepared according to the method described for the compound 5a employing the compound 4c (655 mg, 10 mmol) to afford the compound 5c (450 mg, 68%).
$^1$H NMR (CDCl$_3$) δ 1.23-1.44 (m, 4H), 1.62-1.85 (m, 6H), 2.03-2.19 (m, 3H), 2.29-2.38 (m, 2H), 2.62-2.77 (m, 4H), 3.81-3.92 (m, 4H), 3.95 (s, 3H), 4.18-4.25 (t, 2H, J=6.75 Hz)), 7.44-7.58 (m, 2H), 7.68-7.80 (m, 2H), 7.86-7.93 (m, 2H), 8.75 (s, 1H); MS (FAB) 528 [M+H]+.

Example-4

(2S)—N-{4-[6-[4-piperazinoquinazoline]hexyl]oxy]-5-methoxy-2-nitrobenzoyl}pyrrolidine-2-carboxaldehyde diethylthioacetal (3d)

The compound 3d has been prepared according to the method described for the compound 3a by employing the compounds 1d (563 mg, 10 mmol) was added anhydrous K$_2$CO$_3$ (690 mg, 5.0 mmol) and 4-piperazino-quinazoline (2a) (214 mg, 1.0 mmol) to afford the compound 3d (655 mg, 89%).
$^1$H NMR (CDCl$_3$) δ 1.23-1.39 (m, 6H), 1.52-1.70 (m, 4H), 1.86-1.98 (m, 4H), 2.00-2.05 (m, 4H), 2.13-2.16 (m, 2H), 2.23-2.32 (m, 2H), 2.64-2.85 (m, 4H), 3.20-3.30 (m, 4H), 3.32-3.42 (m, 4H), 3.95 (s, 3H), 4.19-4.24 (t, 2H, J=6.42 Hz), 4.67-4.73 (m, 1H), 4.85-4.87 (d, 1H, J=3.96 Hz), 6.82 (s, 1H), 7.42-7.47 (m, 2H), 7.86-7.91 (m, 3H), 8.71 (s, 1H).
MS (FAB) 697 [M+H]+.

2S)—N-{4-[6-[4-piperazinoquinazoline]hexyl]oxy]-5-methoxy-2-aminobenzoyl}pyrrolidine-2-carboxaldehyde diethylthioacetal (4d)

The compound 4d has been prepared according to the method described for the compound 4a by employing compound 3d (698 mg, 10 mmol) to afford compound 4d (675 mg, 96%), which, due to potential stability problems, was used directly in the next step.

7-Methoxy-8-{5-[4-piperazinoquinazoline]hexyl)-oxy-(11aS)-1,2,3,11a-5H-pyrrolo[2,1-c][1,4]benzodiazepin-5-one (5d)

The compound 5d was prepared according to the method described for the compound 5a employing the compound 4d (668 mg, 10 mmol) to afford the compound 5d (465 mg, 69%).
$^1$H NMR (CDCl$_3$) δ 1.25-1.42 (m, 6H), 1.64-1.88 (m, 6H), 2.02-2.20 (m, 4H), 2.28-2.39 (m, 2H), 2.63-2.78 (m, 4H), 3.80-3.91 (m, 3H), 3.96 (s, 3H), 4.18-4.24 (t 2H, J=6.73 Hz)), 7.42-7.56 (m, 2H), 7.67-7.79 (m, 2H), 7.87-7.94 (m, 2H), 8.74 (s, 1H); MS (ESI) 542 [M+H]+.

Example-5

2S)—N-{4-[8-[4-piperazinoquinazoline]octyl]oxy]-5-methoxy-2-nitrobenzoyl}pyrrolidine-2-carboxaldehyde diethylthioacetal (3e)

The compound 3e has been prepared according to the method described for the compound 3a by employing the compounds 1e (563 mg, 10 mmol) was added anhydrous K$_2$CO$_3$ (712 mg, 5.0 mmol) and 4-piperazino-quinazoline (2a) (214 mg, 1.0 mmol) to afford the compound 3e (675 mg, 90%).
$^1$H NMR (CDCl$_3$) δ 1.23-1.39 (m, 6H), 1.52-1.70 (m, 6H), 1.86-1.98 (m, 4H), 2.00-2.05 (m, 4H), 2.13-2.16 (m, 2H), 2.23-2.32 (m, 2H), 2.64-2.85 (m, 4H), 3.20-3.30 (m, 4H), 3.32-3.42 (m, 4H), 3.95 (s, 3H), 4.19-4.24 (t, 2H, J=6.42 Hz), 4.67-4.73 (m, 1H), 4.85-4.87 (d, 1H, J=3.96 Hz), 6.82 (s, 1H), 7.42-7.47 (m, 2H), 7.86-7.91 (m, 3H), 8.71 (s, 1H).
MS (FAB) 697 [M+H]+.

2S)—N-{4-[6-[4-piperazinoquinazoline]octyl]oxy]-5-methoxy-2-aminobenzoyl}pyrrolidine-2-carboxaldehyde diethylthioacetal (4e)

The compound 4e has been prepared according to the method described for the compound 4a by employing compound 3e (714 mg, 10 mmol) to afford compound 4e (682 mg, 95%), which, due to potential stability problems, was used directly in the next step.

7-Methoxy-8-{5-[4-piperazinoquinazoline]octyl)-oxy-(11aS)-1,2,3,11a-5H-pyrrolo[2,1-c][1,4]benzodiazepin-5-one (5e)

The compound 5e was prepared according to the method described for the compound 5a employing the compound 4e (675 mg, 10 mmol) to afford the compound 5e (481 mg, 72%).
$^1$H NMR (CDCl$_3$) δ 1.25-1.42 (m, 6H), 1.64-1.88 (m, 8H), 2.02-2.20 (m, 4H), 2.28-2.39 (m, 2H), 2.63-2.78 (m, 4H), 3.80-3.91 (m, 3H), 3.96 (s, 3H), 4.18-4.24 (t 2H, J=6.73 Hz)), 7.42-7.56 (m, 2H), 7.67-7.79 (m, 2H), 7.87-7.94 (m, 2H), 8.74 (s, 1H); MS (ESI) 556 [M+H]+.

Biological Activity: some of in vitro biological activity studies were carried out at the National Cancer Institute, Maryland, USA.
Cytotoxicity:
The compounds (5a) 7-Methoxy-8-{4-[-3-(4-piperazinoquinazoline]propyl}-oxy-(11aS)-1,2,3,11a-5H-pyrrolo[2,1-c][1,4]benzodiazepin-5-one.
(5b) 7-Methoxy-8-{4-[-4-(4-piperazinoquinazoline]butyl}-oxy-(11aS)-1,2,3,11a-5H-pyrrolo[2,1-c][1,4]benzodiazepin-5-one.
(5c) 7-Methoxy-8-{5-[-3-(4-piperazinoquinazoline]pentyl}-oxy-(11aS)-1,2,3,11a-5H-pyrrolo[2,1-c][1,4]benzodiazepin-5-one.
(5d) 7-Methoxy-8-{-6-[-3-(4-piperazinoquinazoline]hexyl}-oxy-(11aS)-1,2,3,11a-5H-pyrrolo[2,1-c][1,4]benzodiazepin-5-one.
(5e) 7-Methoxy-8-{8-[-3-(4-piperazinoquinazoline]octyl}-oxy-(11aS)-1,2,3,11a-5H-pyrrolo[2,1-c][1,4]benzodiazepin-5-one were evaluated for in vitro anticancer activity against nine human tumor cells derived from nine cancer types (colon, prostate, oral, lung, cervix and breast cancer) as shown in (Table 1, 2 and 3)

5a, 5c and 5d was evaluated for in vitro anticancer activity against sixty human tumor cells derived from nine cancer types leukemia, non-small-cell lung, colon, CNS, melanoma, ovarian, prostate, and breast cancer) as shown in (Table 1 and 2). For the compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI 0% growth) and 50% cell death (LC50, −50% growth) compared with the control was calculated. The mean graph midpoint values of $\log_{10}$ TGI and $\log_{10}$ LC50 as well as $\log_{10}$ GI50 for 5a is listed in Table 1 and 2). As demonstrated by mean graph pattern, compound 5c and 5d exhibited an interesting profile of activity and selectivity for various cell lines. The mean graph mid point of $\log_{10}$ TGI and $\log_{10}$ LC50 showed similar pattern to the $\log_{10}$ GI50 mean graph mid points.

TABLE 1

Log $GI_{50}$ (concentration in mol/L causing 50% growth inhibition) values for quinazoline-PBD hybrids.

| Cancer Cell Lines | 5a | 5c | 5d |
|---|---|---|---|
| Leukemia | −5.68 | −5.58 | −5.49 |
| Non-small cell lung | −5.82 | −5.38 | −4.87 |
| Colon | −5.55 | −5.76 | −5.41 |
| CNS | −4.86 | −5.61 | −4.63 |
| Melanoma | −5.65 | −5.38 | −5.29 |
| Ovarian | −5.56 | −4.60 | −4.28 |
| Renal | −5.67 | −5.39 | −5.17 |
| Prostate | −4.63 | −5.05 | −5.85 |
| Breast | −5.57 | −4.31 | −4.52 | each cancer type represents the average of six to eight different cancer cell lines. In vitro evaluation of cytotoxic activity: Among them 5a exhibits a wide spectrum of activity against sixty cell lines in nine cell panels, with $GI_{50}$ value of <20 nM. In the non-small cell lung cancer panel, the growth of HOP-62, NCI-H23 cell lines were affected by compound 5a with $GI_{50}$ values as 11.4, 14.6 and 19.7 nM respectively. The $GI_{50}$ values of compound 5a against colon cancer HCC-2988, HCT-116 and KM12 cell lines are 11.3, 11.8 and 11.7 nM respectively. The $GI_{50}$ values for compound 5a against CNS SF-295, SF-539, SNB-19 and SNB-75 cell lines are in a range of 12.6-23.9 nM. Four cancer cell lines (OVCAR-4, OVCAR-5, OVCAR-8 and SK-OV-3) in the ovarian cancer cell panel were affected by compound 5a with $GI_{50}$ values of 31.6, 15.1, 30.5 and 79.8 nM respectively. In this study compound 5c exhibited cytotoxicity activity against renal and breast cancer panels with $GI_{50}$ values (11.6-43.4 nM). Compound 5c exhibits activity against sixty cell lines in nine cancer cell panels with $GI_{50}$ values of <10 µM. Compound 5d exhibits activity against fifty-seven cell lines in nine cancer cell panels, $GI_{50}$ values of <10 µM. Cytotoxicity of compounds 5a, 5c and 5d in selected cancer cell lines has been illustrated in Table 1, 2 and 3. Table 2. The average $GI_{50}$ values for each cancer panel of compounds 5a, 5c, and 5d have been illustrated in Table 1, 2 and 3.

TABLE 2

Cytotoxicity of compounds 5a, 5c and 5d in selected cancer cell lines

| Cancer panel/cell line | $GI_{50}$ (µM) 5a | $GI_{50}$ (µM) 5c | $GI_{50}$ (µM) 5d |
|---|---|---|---|
| Leukemia | | | |
| CCRF-CEM | 12.0 | 32.5 | 13.4 |
| HL-60 (TB) | 13.0 | 65.2 | 19.5 |
| RPMI-8226 | 10.0 | 45.0 | 16.8 |
| Non-small cell lung | | | |
| NCI-H226 | 10.0 | 17.8 | 18.4 |
| NCI-H23 | 13.9 | 15.8 | 22.5 |
| NCI-H522 | 10.4 | 65.3 | 18.3 |
| Colon | | | |
| HCT-116 | 11.9 | 21.0 | 14.6 |
| HCT-15 | 27.5 | 29.7 | 18.4 |
| SW-620 | 11.7 | 17.6 | 25.9 |
| CNS | | | |
| SF-539 | 12.6 | 30.3 | 33.7 |
| U251 | 10.0 | 15.8 | 19.8 |
| Melanoma | | | |
| LOX IMVI | 10.0 | 18.2 | 15.0 |
| MALME-3M | 18.2 | 24.2 | 36.2 |
| M14 | 10.1 | 14.5 | 18.8 |
| SK-MEL-5 | 10.0 | 20.9 | 23.3 |
| UACC-257 | 70.9 | 22.9 | 15.9 |
| UACC-62 | 10.0 | 15.1 | 22.5 |
| Ovarian | | | |
| OVCAR-3 | 10.0 | 24.9 | 26.3 |
| Renal | | | |
| 786-0 | 11.8 | 18.4 | 14.9 |
| A498 | 16.1 | 20.1 | 22.0 |
| ACHN | 43.4 | 22.0 | 46.1 |
| CAKI-1 | 13.6 | 25.8 | 12.9 |
| TK-10 | 16.6 | 38.2 | 31.4 |
| UO-31 | 13.2 | 22.1 | 15.2 |
| Breast | | | |
| NCI/ADR-RES | 13.4 | 17.7 | 18.7 |
| MDA-MB-231/ATCC | 11.6 | 19.9 | 14.2 |

The mean graph mid point values of $\log_{10}$ TGI and $\log_{10}$ $LC_{50}$ as well as $\log_{10}$ $GI_{50}$ for 5a, 5c and 5d are listed in Table-3. As demonstrated by mean graph pattern, compounds 5a, 5c and 5d exhibit an interesting profile of activity and selectivity for various cell lines. The mean graph mid points of $\log_{10}$ TGI and $\log_{10}$ $LC_{50}$ have shown similar pattern to the $\log_{10}$ $GI_{50}$ mean graph mid points.

TABLE 3

$\log_{10}$ $GI_{50}$, $\log_{10}$ TGI and $\log_{10}$ $LC_{50}$ mean graphs midpoints (MG_MID) of In vitro cytotoxicity data for the compounds 5a, 5c and 5d against human tumor cell lines.

| Compound | $\log_{10} GI_{50}$ | $\log_{10}$ TGI | $\log_{10} LC_{50}$ |
|---|---|---|---|
| 5a | −7.68 | −6.66 | −4.99 |
| 5c | −5.68 | −4.86 | −4.19 |
| 5d | −6.49 | −5.85 | −4.96 |

ADR = Adiramycin is the control drug

Thermal Denaturation Studies

Compounds were subjected to thermal denaturation studies with duplex-form calf thymus DNA (CT-DNA) using an adaptation of a reported procedure. Working solutions in aqueous buffer (10 mM $NaH_2PO_4/Na_2HPO_4$, 1 mM $Na_2EDTA$, pH 7.00+0.01) containing CT-DNA (100 µm in phosphate) and the PBD (20 µm) were prepared by addition of concentrated PBD solutions in DMSO to obtain a fixed [PBD]/[DNA] molar ratio of 1:5. The DNA-PBD solutions were incubated at 37° C. for 0, 18, and 36 h prior to analysis. Samples were monitored at 260 nm using a Beckman DU-7400 spectrophotometer fitted with high performance temperature controller, and heating was applied at 1° C. min$^{-1}$ in the 40-90° C. range. DNA helix coil transition temperatures (Tm) were obtained from the maxima in the (dA260)/dT derivative plots. Results are given as the mean±standard deviation from three determinations and are corrected for the effects of DMSO co-solvent using a linear correction term. Drug-induced alterations in DNA melting behaviour are given by: ΔTm=Tm(DNA+PBD)−Tm (DNA alone), where the Tm value for the PBD-free CT-DNA is 69.0±0.01. The fixed [PBD]/[DNA] ratio used did not result in binding saturation of the host DNA duplex for any compound examined. Compound 5a, 5c and 5d at 0 hr, 18 hr and 36 hr gradually increased at 37° C.

TABLE 4

Thermal denaturation data of C8-linked quinazoline hybrids of pyrrolo[2,1-c]-[1,4]benzodiazepine with calf thymus (CT) DNA

| PBD hybrids | [PBD]:[DNA] molar ratio[b] | ΔT$_m$ (° C.)[a] after incubation at 37° C. for | |
|---|---|---|---|
| | | 0 h | 18 h |
| 5a | 1:5 | 9.2 | 10.4 |
| 5b | 1:5 | 9.7 | 10.9 |
| 5c | 1:5 | 10.3 | 11.8 |
| 5d | 1:5 | 10.6 | 12.2 |
| DC-81 | 1:5 | 0.3 | 0.7 |

[a]For CT-DNA alone at pH 7.00 ± 0.01, T$_m$ = 68.5° C. ± 0.01 (mean value from 10 separate determinations), all ΔT$_m$ values are ± 0.1-0.2° C.

For a 1:5 molar ratio of [PBD]/[DNA], where CT-DNA concentration = 100 μM and ligand concentration = 20 μM in aqueous sodium phosphate buffer [10 mM sodium phosphate + 1 mM EDTA, pH 7.00 ± 0.01].

The ΔT$_m$ for PBD hybrids 5a, 5b, 5c and 5d at a [PBD]:[DNA] molar ratio of 1:5 increased to a value of 10.4° C., 10.9° C., 11.8 and 12.2° C. after 18 h incubation respectively.

The DNA binding activity for these novel C8-linked quinazoline-PBD hybrids has been examined by thermal denaturation studies using calf thymus (CT) DNA. Melting studies show that these compounds stabilize the thermal helix→coil or melting stabilization (ΔT$_m$) for the CT-DNA duplex at pH 7.0, incubated at 37° C., where PBD/DNA molar ratio is 1:5. Interestingly, in this assay one of the quinazoline-PBD hybrid (5a-d) elevates the helix melting temperature of CT-DNA by a margin of 12.2° C. after incubation for 18 h at 37° C. Data for 5a-d and DC-81 are included in Table 4 for comparison.

ADVANTAGES OF THE INVENTION

1. The present invention provides a new pyrrolo[2,1-c][1,4]benzodiazepine hybrids useful as antitumour agents.

2. It also provides a process for the preparation of novel pyrrolo[2,1-c][1,4]benzodiazepine hybrids

We claim:

1. A compound of formula 5

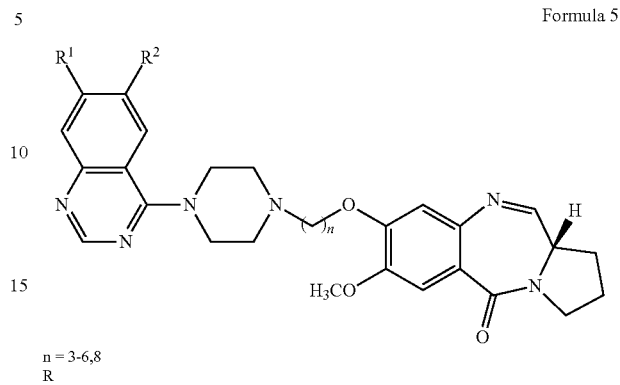

Formula 5 n = 3-6,8 wherein, n=3-6 or 8 and wherein R$^1$ and R$^2$ is selected from the group consisting of R$^1$=H, R$^2$=H or R$^1$=CH$_3$O, R$^2$=CH$_3$O or R$^1$=CH$_3$O and R$^2$=C$_2$H$_5$O.

2. The compound according to claim 1 selected from the group consisting of:

7-Methoxy-8-{[-3-(4-piperazinoquinazoline]propyl}-oxy-(11aS)-1,2,3,11a-5H-pyrrolo[2,1-c][1,4]benzodiazepin-5-one (5a);

7-Methoxy-8-{[-4-(4-piperazinoquinazoline]butyl}-oxy-(11aS)-1,2,3,11a-5H-pyrrolo[2,1-c][1,4]benzodiazepin-5-one (5b);

7-Methoxy-8-{[-5-(4-piperazinoquinazoline]pentyl}-oxy-(11aS)-1,2,3,11a-5H-pyrrolo[2,1-c][1,4]benzodiazepin-5-one (5c);

7-Methoxy-8-{[-6-(4-piperazinoquinazoline]hexyl}oxy-(11aS)-1,2,3,11a-5H-pyrrolo[2,1-c][1,4]benzodiazepin-5-one (5d);

7-Methoxy-8-{[-8-(4-piperazinoquinazoline]octyl}-oxy-(11aS)-1,2,3,11a-5H-pyrrolo[2,1-c][1,4]benzodiazepin-5-one (5e);

7-Methoxy-8-{6,7-dimethoxy[-3-(4-piperazinoquinazoline]propyl}-oxy-(11aS)-1,2,3,11a-5H-pyrrolo[2,1-c][1,4]benzodiazepin-5-one (5f);

7-Methoxy-8-{6,7-dimethoxy[-4-(4-piperazinoquinazoline]butyl}-oxy-(11aS)-1,2,3,11a-5H-pyrrolo[2,1-c][1,4]benzodiazepin-5-one (5g);

7-Methoxy-8-{6,7-dimethoxy[-5-(4-piperazinoquinazoline]pentyl}-oxy-(11aS)-1,2,3,11a-5H-pyrrolo[2,1-c][1,4]benzodiazepin-5-one (5h);

7-Methoxy-8-{6,7-dimethoxy[-6-(4-piperazinoquinazoline]hexyl}-oxy-(11aS)-1,2,3,11a-5H-pyrrolo[2,1-c][1,4]benzodiazepin-5-one (5i);

7-Methoxy-8-{6,7-dimethoxy[-8-(4-piperazinoquinazoline]octyl}-oxy-(11aS)-1,2,3,11a-5H-pyrrolo[2,1-c][1,4]benzodiazepin-5-one (5j);

7-Methoxy-8-{7-ethoxy,6-methoxy[-3-(4-piperazinoquinazoline]propyl}-oxy-(11aS)-1,2,3,11a-5H-pyrrolo[2,1-c][1,4]benzodiazepin-5-one (5k);

7-Methoxy-8-{7-ethoxy,6-methoxy[-4-(4-piperazinoquinazoline]butyl}-oxy-(11aS)-1,2,3,11a-5H-pyrrolo[2,1-c][1,4]benzodiazepin-5-one (5l);

7-Methoxy-8-{7-ethoxy,6-methoxy[-5-(4-piperazinoquinazoline]pentyl}-oxy-(11aS)-1,2,3,11a-5H-pyrrolo[2,1-c][1,4]benzodiazepin-5-one (5m);

7-Methoxy-8-{7-ethoxy,6-methoxy[-6-(4-piperazinoquinazoline]hexyl}-oxy-(11aS)-1,2,3,11a-5H-pyrrolo[2,1-c][1,4]benzodiazepin-5-one (5n); and 7-Methoxy-8-{7-ethoxy,6-methoxy[-8-(4-piperazino-quinazoline]octyl}-oxy-(11aS)-1,2,3,11a-5H-pyrrolo[2,1-c][1,4]benzodiazepin-5-one (5o).

3. A pharmaceutical composition comprising a compound of Formula 5 according to claim 1 and one or more pharmaceutically acceptable carriers, adjuvants or additives.

4. A process for the preparation of quinazoline linked pyrrolo[2,1-c][1,4]benzodiazepine hybrid of formula 5,

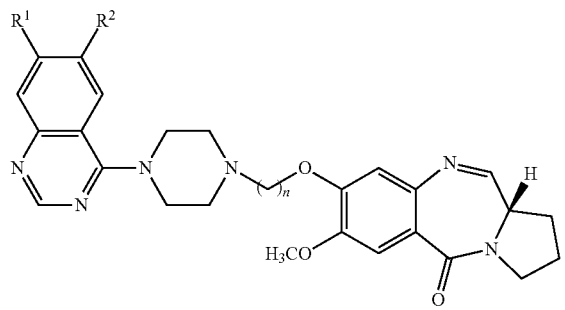

n = 3-6,8
R wherein n=3, 4, 5, 6, 8 and wherein $R^1$ and $R^2$ is selected from the group consisting of $R^1$=H, $R^2$=H or $R^1$=CH$_3$O, $R^2$=CH$_3$O or $R^1$=CH$_3$O and $R^2$=C$_2$H$_5$O the said process comprising the steps of:

a) reacting (2S)—N-[4-(n-bromoalkyl)oxy-5-methoxy-2-nitrobenzoyl]pyrrolidine-2-carboxaldehyde diethylthioacetal of formula 1

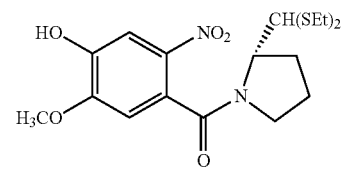

with substituted and un substituted piperazinoquinazoline derivative selected from the compound of formula 2

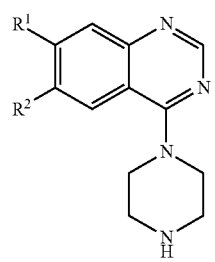

2 and wherein $R^1$ and $R^2$ is selected from the group consisting of $R^1$=H, $R^2$=H or $R^1$=CH$_3$O, $R^2$=CH$_3$O or $R^1$=CH$_3$O and $R^2$=, in the presence of a mild inorganic base, in an aprotic organic solvent, under refluxing temperature to obtain the resultant nitro compound of (2S)—N-{4-[n-[4-piperazinoquinazoline]alkyl]oxy]-5-methoxy-2-nitrobenzoyl}pyrrolidine-2-carboxaldehyde diethylthioacetal of formula 3a-o

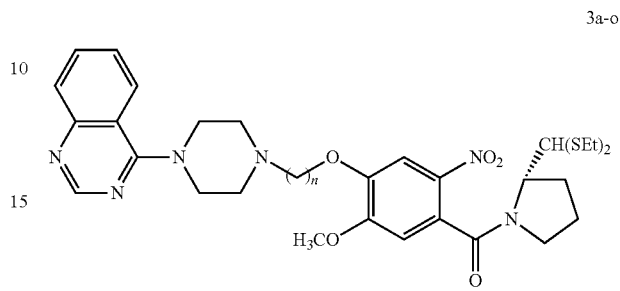

3a-o wherein $R^1$ and $R^2$ is selected from the group consisting of $R^1$=H, $R^2$=H or $R^1$=CH$_3$O, $R^2$=CH$_3$O or $R^1$=CH$_3$O and $R^2$=C$_2$H$_5$O b) reducing (2S)—N-{4-[n-[4-piperazinoquinazoline]alkyl]oxy]-5-methoxy-2-nitro benzoyl}pyrrolidine-2-carboxaldehyde diethylthioacetal of formula 3 with SnCl$_2$.2H$_2$O, in an alcohol, under reflux, followed by the evaporation of alcohol and adjusting the pH of the resultant product layer to about 8 by using a base, followed by extraction with ethyl acetate and washing the combined organic phase with brine solution and evaporating the solvent to obtain the desired (2S)—N-{-4-[n-[4-Piperazinoquinazoline]alkyl]oxy]-5-methoxy-2-amino benzoyl}pyrrolidine-2-carboxaldehyde diethylthioacetal 4a-o,

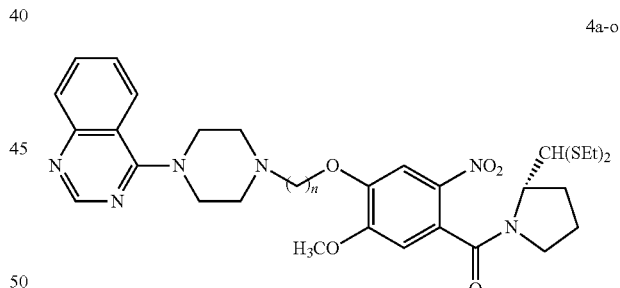

4a-o wherein $R^1$, $R^2$=H, OCH$_3$, OC$_2$H$_5$ c) reacting (2S)—N-{-4-[5-[4-piperazinoquinazoline]pentyl]oxy]-5-methoxy-2-aminobenzo-yl}pyrrolidine-2-carboxaldehyde diethylthioacetal of formula 4 with mercuric chloride, in a mixture of water and organic solvent, in the presence of mild inorganic basic compound, under stirring, at a temperature of about 20-30° C., for a period of 8-12 hrs, followed by the extraction of yellow organic supernatant and washing with sodium bi carbonate and brine, respectively, and evaporating the organic layer, under reduced pressure and further purified by column chromatography to obtain the desired product of quinazoline linked pyrrolo[2,1-c][1,4]benzodiazepine hybrid of formula 5a-o

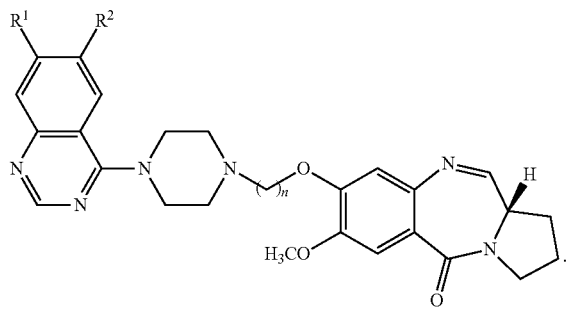

n = 3-6,8
R¹ & R² = H, OCH₃•OC₂H₅

5a-o

5. The process according to claim 4, wherein the mild inorganic base used in steps (a) is potassium carbonate.

6. The process according to claim 4, wherein the aprotic organic solvent used in step (a) is acetone and acetonitrile.

7. The process according to claim 4, wherein the organic solvent used in step (c) is acetonitrile and acetone.

8. The process according to claim 4, wherein the alcohol used in step (b) is selected from methanol and ethanol.

9. A method of treating cancer wherein the cancer is selected from the group consisting of non-small cell lung, colon, CNS, melanoma, ovarian renal, prostate and breast cancers comprising administering a compound of Formula 5 according to claim 1 to a subject in need thereof.

\* \* \* \* \*